United States Patent [19]

Martin

[11] Patent Number: 4,897,109
[45] Date of Patent: Jan. 30, 1990

[54] COMPOSITIONS FOR PROTECTING CULTURE PLANTS FROM THE PHYTOTOXIC ACTION OF HERBICIDALLY ACTIVE CHLORACETANILIDES

[75] Inventor: Henry Martin, Basel, Switzerland

[73] Assignee: Ciba-Geigy Corporation, Ardsley, N.Y.

[21] Appl. No.: 106,985

[22] Filed: Oct. 5, 1987

Related U.S. Application Data

[63] Continuation of Ser. No. 668,607, Nov. 6, 1984.

[30] Foreign Application Priority Data

May 28, 1984 [CH] Switzerland .......................... 2612/84

[51] Int. Cl.$^4$ ..................... A01N 29/00; A01N 29/10; A01N 25/32
[52] U.S. Cl. .......................... 71/118; 71/111; 71/115; 71/98; 71/103; 71/88; 71/105; 71/90; 71/92; 47/57.6; 560/9; 560/12; 560/16; 560/27; 560/29; 549/370; 549/373; 549/407; 549/473; 549/494; 549/435; 549/441; 564/212; 564/207
[58] Field of Search .................... 564/212, 207; 71/77, 71/118; 47/57.6

[56] References Cited

U.S. PATENT DOCUMENTS

| 2,732,403 | 1/1956 | Surrey | 564/212 |
|---|---|---|---|
| 2,852,562 | 9/1958 | Surrey | 564/212 X |
| 2,912,438 | 11/1959 | Oxley et al. | 564/212 X |
| 2,929,844 | 3/1960 | Surrey | 564/212 |
| 3,071,613 | 1/1963 | Surrey | 564/212 X |
| 3,504,028 | 3/1970 | Beregi et al. | 564/212 |
| 3,733,339 | 5/1973 | Horron | 260/340.5 |
| 3,867,444 | 2/1975 | Baker | 71/118 X |
| 3,937,730 | 2/1976 | Vogel et al. | 71/118 |
| 3,950,335 | 4/1976 | Schromm et al. | 564/212 X |
| 4,021,224 | 5/1977 | Pallos et al. | 564/212 X |
| 4,033,756 | 7/1977 | Hoffmann | 71/100 |
| 4,070,389 | 1/1978 | Martin | 260/465 E |
| 4,124,376 | 11/1978 | Pallos et al. | 71/118 |
| 4,137,070 | 1/1979 | Pallos et al. | 71/100 |
| 4,208,203 | 6/1980 | Hoffmann | 71/118 |
| 4,269,618 | 5/1981 | Pallos et al. | 71/88 |
| 4,274,862 | 6/1981 | Kirino et al. | 564/212 X |
| 4,288,244 | 9/1981 | Kirino et al. | 564/212 X |
| 4,294,764 | 10/1981 | Rinehart | 71/88 |
| 4,345,935 | 8/1982 | Thibault | 71/92 |
| 4,414,224 | 11/1983 | Huffman et al. | 424/274 |

FOREIGN PATENT DOCUMENTS

| 229741 | 1/1959 | Australia | 564/212 |
|---|---|---|---|
| 535830 | 3/1955 | Belgium . | |
| 569109 | 1/1959 | Belgium . | |
| 140271 | 5/1985 | European Pat. Off. . | |
| 2141586 | of 1970 | Fed. Rep. of Germany . | |
| 2218097 | of 1971 | Fed. Rep. of Germany . | |
| 2402983 | of 1973 | Fed. Rep. of Germany . | |
| 2828265 | of 1980 | Fed. Rep. of Germany . | |
| 2828293 | of 1980 | Fed. Rep. of Germany . | |
| 3004871 | 8/1981 | Fed. Rep. of Germany . | |
| 26847 | 11/1969 | Japan | 564/212 |
| 9934 | 4/1970 | Japan | 564/212 |
| 26853 | 3/1981 | Japan | 564/212 |
| 29751 | 2/1983 | Japan | 564/212 |
| 29752 | 2/1983 | Japan | 564/212 |
| 103350 | 6/1983 | Japan | 564/212 |
| 747592 | 4/1956 | United Kingdom | 564/212 |
| 1454043 | of 1976 | United Kingdom . | |
| 2078521 | 1/1982 | United Kingdom . | |

OTHER PUBLICATIONS

CA 58:6721(c)–6722(e) (1963).
CA 58:2402(e) (1963).
CA 56:10006(g) (1962).
Kidd et al., J. Chem. Soc. vol. 1962 pp. 1426–1427.
CA 60: 4136(g) (1963).
Hanada et al., Chem. Pharm. Bull. vol. 29 pp. 128–136 (1981).
Chem. Abstract, 92, 210191 (1980).
Hasan et al., Indian J. Chem. vol. 9, Sept. 1971, No. 9 pp. 1022–4.

Primary Examiner—Glennon H. Hollrah
Assistant Examiner—K. Konstas
Attorney, Agent, or Firm—Edward McC. Roberts

[57] ABSTRACT

A composition for protecting culture plants from the phytotoxic action of herbicidally active chloracetanilides contains as active ingredient an acylamine derivative of the formula I $$\underset{(QX)_n}{\overset{Z}{\diagdown}} \text{—} A\text{—}\underset{B}{\overset{|}{N}}\text{—}COR_1$$

wherein
X is oxygen, sulfur, —SO— or —SO$_2$—,
Q is an alkyl, alkenyl, alkinyl group, which may be interupted by oxygen, sulfur, sulfinyl or sulfonyul, or a test 1,3-dioxolan-2-yl-alkyl, 1,3-dioxolan-4-alkyl, 2,2-dialkyl-1,3-dioxolan-4-ylalkyl, 1,3-dioxan-2-ylalkyl, 2-benzopyranylalkyl, alkoxycarbonyl alkenyloxycarbonyl or tetrahydrofurylalkyl, or the group
OX represents also a halogenoalkyl radical,
n is 1, 2 or 3,
Z is hydrogen, halogen, alkyl or dioxymethylene,
A is a C$_1$-C$_8$ -hydrocarbon radical which may be staight-chained, branched or cyclic and which is unsubstituted or substituted by alkoxy, alkylthio, cyano or halogen,
B is hydrogen, a C$_1$-C$_6$-hydrocarbon radical which may be saturated or olefinic, substituted or unsubstituted or B may be cycloalkyl, alkylcycloalkyl, 1,3-dioxolan-2-ylalkyl, 1,3-dioxolan-4-ylalkyl, 1,3-dioxan-2-ylalkyl, furylalkyl, tetrahydrofurylalkyl or a radical —NH—COOR, —CH$_2$COOR or CH(CH$_3$)COOR, wherein
R is C$_1$-C$_3$-alkyl or allyl and
R$_1$ is halogenoalky or halogenoalkenyl.

Some of these compounds are new. They protect culture plants such as cereal, maize, millet and rice from the phytotoxic action of the chloracetanilide without reducing the herbicidal action on the weeds.

13 Claims, No Drawings

COMPOSITIONS FOR PROTECTING CULTURE PLANTS FROM THE PHYTOTOXIC ACTION OF HERBICIDALLY ACTIVE CHLORACETANILIDES

This application is a continuation, of application Ser. No. 668,607, filed 11/6/84.

The present invention relates to a composition for protecting culture plants from the phytotoxic action of herbicidally active chloracetanilides, which contains as active ingredient capable of antagonizing the phytotoxic action of the herbicide an acylamide derivative, the invention further relates to compositions, which contain a herbicide and the herbicide-antagonizing acylamide derivative and to a process for selectively controlling weeds by means of these herbicides and antagonizing agents. The invention relates also to the production of the acylamide derivatives.

It is known that herbicides belonging to a very wide range of compound classes such as triazines, urea derivative, carbamatates, thiocarbamates, haloacetanilides, halophenoxyacetic acids etc., when employed in an effective concentration, often also damage cultivated plants to a certain extent in addition to the weeds which it is desired to control. Too high concentrations are often applied unintentionally and randomly whenever peripheral zones overlap on zonal spraying, whether as a consequence of the action of wind or through miscalculating the sweep of the spray device employed. The climatic conditions or the nature of the soil may be such that the concentration of herbicide recommended for normal conditions acts as an overdose. The quality of the seeds may also be a factor in the tolerance of the herbicide. To counteract this problem, different compounds have already been proposed which are able specifically to antagonise the harmful action of the herbicide on the cultivated plant, i.e. to protect the cultivated plant without noticeably influencing the herbicidal action on the weeds to be controlled. However, it has been found that the proposed antidotes very often have a species-specific activity both with respect to the cultivated plants and to the herbicide and also, in some cases, contingent on the mode of application, i.e. a specific antidote is often suitable only for a specific cultivated plant and a few classes of herbicides.

The direct pre- or postemergence treatment of certain useful plants with antidotes as antagonist of specific classes of herbicides in a crop area is disclosed in German Offenlegungsschrift specifications 2 141 586 and 2 218 097 and in U.S. patent specification 3 867 444.

Further, German Offenlegungsschrift 2 402 983 discloses that maize plants can be effectively protected against damage by chloroacetanilides by adding an N-disubstituted dichloroacetamide as antidote to the soil. These compounds can also be used as antidotes with herbicidally active thiocarbamates according to U.S. Pat. No. 4 137 070 or as antidotes against herbicidally active acetanilides according to German Offenlegungschriften 2 828 265 and 2 828 293.

It has now be found that surprisingly a group of acylamide derivatives is extraordinary well suited to protect culture plants from the harmful effects of agrochemicals, such as plant-protection compounds, especially herbicides. These acylamide derivatives will be termed further on as "antagonizing agents", "antidotes" or "safeners".

The acylamide derivatives, e.g. halogenated phenylalkylamines which are effective for protecting culture plants form the harmful effect of herbicidally active choracetanilides correspond to the formula I

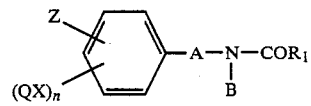

wherein
X is oxygen, sulfur a group —SO— or —SO$_2$—,
Q is alkyl, alkenyl, alkinyl, cycloalkyl, alkoxyalkyl, alkenyloxyalkyl, alkinyloxyalkyl, alkylthioalkyl, alkenylthioalkyl, alkinylthioalkyl, alkylsulfinylalkyl, alkylsulfonylalkyl, halogenoalkyl, cyanoalkyl, 2,2-dialkoxyalkyl, 1,3-dioxolan-2-ylalkyl, 1,3-dioxolan-4-ylalkyl, 2,2-dialkyl-1,3-dioxolan-4-ylalkyl, 1,3-dioxan-2-ylalkyl, 2-benzopyranylalkyl, alkoxycarbonyl, alkenyloxycarbonyl or tetrahdrofurylalkyl, the group Q-X represents also a halogenoalkyl radical;
n is 1,2, or 3,
Z is hydrogen, halogen, alkyl or dioxymethylene;
A is a C$_1$-C$_8$-hydrocarbon radical, which may be straight-chained, branched or cyclic and which is unsubstituted or substituted by alkoxy, alkylthio, cyano or halogen,
B is hydrogen, a C$_1$-C$_6$ hydrocarbon radical, which may be saturated or olefinic and is unsubstituted or substituted by alkoxy, polyalkoxy, halogen, cyano or trifluoromethyl; or B may be cycloalkyl, alkylcycloalkyl, dialkoxyalkyl, 1,3-dioxolan-2-ylalkyl, 1,3-dioxolan-4-alkyl, 1,3-dioxan-2-ylalkyl, furylalkyl, tetrahydrofurylalkyl or a radical —NHCOOR, —CH$_2$COOR or CH(CH$_3$)COOR whereby
R is C$_1$-C$_3$-alkyl or allyl and
R$_1$ is halogenoalkyl or halogenoalkenyl.

The compounds of formula I may exist in isomeric optically active forms. This invention relates to the optically pure isomers as well as to the mixtures of isomers in which the compounds of formula I may occur.

Halogen itself or where it occurs in the definitions as part of halogenalkyl, halogenalkoxy or halogenalkenyl signifies fluorine, chlorine, bromine or iodine, whereby fluorine and bromine but especially chlorine are preferred.

Alkyl may in the definitions be straight-chain or branched and be represented by the following residues; e.g. methyl, ethyl, n-propyl, isopropyl, or the isomeric forms of butyl, pentyl or hexyl.

Under alkoxy is to be understood e.g. methoxy, ethoxy, n-propyloxy, isopropyloxy or the isomeric butyloxy, pentyloxy or hexyloxy radicals especially however methoxy, ethoxy or isopropyloxy.

Examples for unsaturated substituents or part of such substituents are e.g. vinyl, vinyloxy, allyl, allyloxy, propinyl, propinyloxy, methallyl, methallyloxy, butenyl, butenyloxy, butynyl, butynyloxy, chlorovinyl, chlorovinyloxy, dichlorovinyl, trichlorovinyl, 3,3,3-trifluoro-1-propenyl, 3,3,3-trichloro-1-propynyl or 2,3-dichloropropenyl.

Alkoxyalkoxy radicals are represented e.g. by methoxymethyl, ethoxymethyl, methoxyethyl, propyloxyethyl, isopropyloxyethyl, butyloxyethyl, allyloxyethyl, preferred is methoxyethyl.

Halogenoalkyl alone or as part of a substituent like halogenoalkoxy or halogenoalkylthio is represented by radicals like chloromethyl, fluoromethyl, difluoromethyl, trifluoromethyl, dichloromethyl, trichloromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 2-chloropropyl, 1,1,2,3,3,3-hexafluoropropyl, 3,3,3-trichloropropyl, 2,2,2-trichloroethyl, 1-chlorethyl, preferred are chloromethyl, dichloromethyl, trichloromethyl and 1-chloroethyl.

Because of their pronounced activity as herbicide-antagonists, the following acylamide derivatives of the formula I have especially been noted, wherein
(a) X represents oxygen,
(b) Q is $C_1$-$C_6$-alkyl, 2,2-dialkoxyalkyl or 1,3-dioxolan-2-ylalkyl,
(c) n is 1 or 2,
(d) Z is hydrogen,
(e) X-Q represents trifluoromethyl,
(f) A is a bridging group

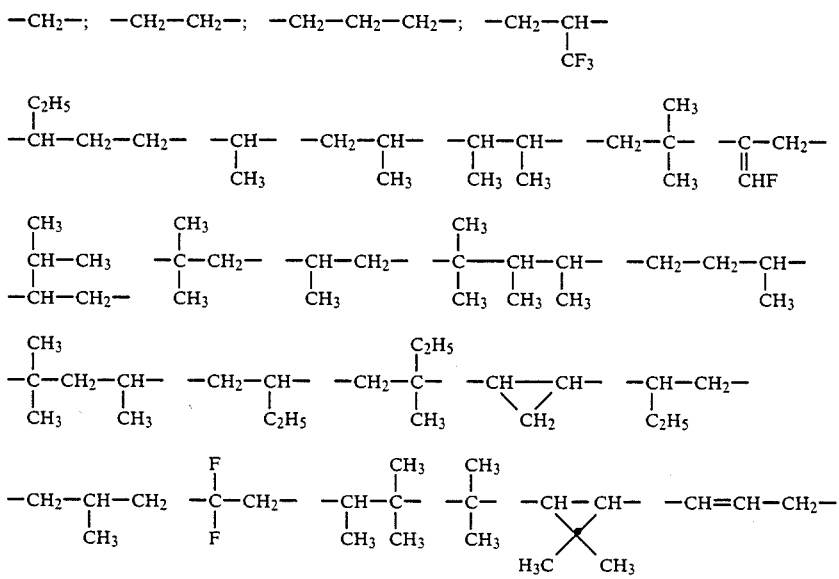

(g) B is hydrogen, $C_1$-$C_6$-alkyl, $C_2$-$C_6$-alkenyl, $C_1$-$C_4$-alkoxy, tetrahydrofurfurylmethyl or —NH—COOC$_2$H$_5$ or —CH$_2$—COOC$_2$H$_5$
(h) $R_1$ is $C_1$-$C_6$-halogenoalkyl Among the active substances of group (b) those are preferred, wherein Q is $C_1$-$C_3$-alkyl, 1,3-dioxolan-2-ylmethyl and 2,2-dimethoxyethyl and among group (f) those, where A is a bridging group

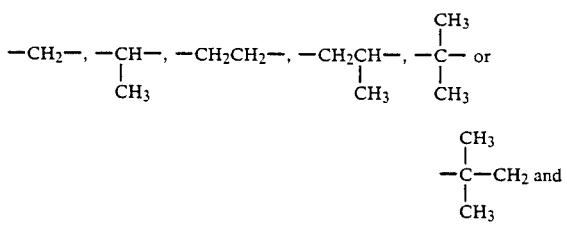

of among group (g) those active substances are preferred wherein B is hydrogen, $C_1$-$C_4$-alkyl or $C_2$-$C_4$-alkenyl.

An especially important group of active substances represent those wherein X is oxygen, Q is methyl, n is 1 or 2, X-P is trifluoromethyl, Z is hydrogen, A is selected among —CH$_2$—, —CH$_2$—CH$_2$—, CH$_2$CH(CH$_3$)— and $X_1$ is methyl, ethyl, propyl, isopropyl, isobutyl, sec.butyl and allyl and $R_1$ is $C_1$-$C_3$-dihaloalkyl.

The preferred compounds are
N-(3,4-dimethoxyphenylethyl)-N-isopropyl-dichloroacetamide,
N-(3,4-dimethoxyphenylethyl)-N-isopropyl-chloroacetamide,
N-(3,4-dimethoxyphenylethyl)-N-sec.butyl-dichloroacetamide,
N-(3,4-dimethoxybenzyl)-N-isopropyl-dichloroacetamide,
N-(3,4-methoxybenzyl)-N-n-propyl-dichloroacetamide,
N-(3,4-methoxybenzyl)-N-(2-methoxyethyl)-dichloroacetamide,
N-(3,4-methoxybenzyl)-N-isopropyl-(2-chloropropionyl)amide,
N-4-methoxybenzyl-N-isopropyl-dichloroacetamide,
N-4-trifluoromethylbenzyl-N-isopropyl-dichloroacetamide,
N-(4-ethoxy-3-methoxybenzyl)-N-isopropyl-dichloroacetamide,
N-[2-(4-methoxyphenyl)-1-methyl-ethyl]-N-isopropyl-dichloroacetamide,
$N^1$-(3,4-dimethoxybenzyl)-$N^1$-dichloroacetyl-$N^2$-ethoxycarbonylhydrazide,
N-(3-methoxybenzyl)-N-isopropyl-dichloroacetamide,
N-(2-methoxybenzyl)-N-isopropyl-dichloroacetamide,
N-(3,4-dimethoxybenzyl)-N-isobutyl-dichloroacetamide,
N-(3,4,5-trimethoxybenzyl)-N-isopropyl-dichloroacetamide,
N-[2-(4-methoxyphenyl)-1-methyl-]ethyl-chloroacetamide,
N-(2,4-dimethoxybenzyl)-N-isopropyl-dichloroacetamide,
N-(2,5-dimethoxybenzyl)-N-isopropyl-dichloroacetamide,
N-(2,3-dimethoxybenzyl)-N-isopropyl-dichloroacetamide,
N-(3,5-dimethoxybenzyl)-N-isopropyl-dichloroacetamide, N-(4-methoxybenzyl)-N-(2′,2′-dimethoxyethyl)-dichloroacetamide,
N-(4-methoxybenzyl)-N-ethyl-dichloroacetamide,
N-(4-trifluorobenzyl)-chloroacetamide,
N-(3,4-dimethoxybenzyl)-N-sec.butyl-dichloroacetamide,
N-(3,4-dimethoxybenzyl)-N-allyl-dichloroacetamide,
N-(4-methoxybenzyl)-dichloroacetamide,
N-(3,4,5-trimethoxyphenylethyl)-N-isopropyl-dichloroacetamide,
N-[4-(1,3-dioxolan-2-yl-methoxy)benzyl]dichloroacetamide,
N-[4-(1,3-dioxolan-2-yl-methoxy)benzyl]-N-isopropyl-dichloroacetamide.

The compounds of the formula I are new products with the exception of N-(4-methoxybenzyl)-dichloroacetamide, which is known from U.S. Pat. No. 4,208,203. This compound is mentioned there among others as a safener for protecting maize-cultures from the phytotoxic action of thiolcarbamate-herbicides. Further are known N-(3,4-methylendioxybenzyl-dichloroacetamide and N-benzyl-N-isopropyl-dichloroacetamide from U.S. Pat. No. 4,137,070 where they are disclosed as safeners against thiolcarbamate-herbicides and from U.S. Pat. No. 4 124 376 where they are mentioned as safeners against chloracetanilide-herbicides.

It is surprising and was not predictable that N-(4-methoxybenzyl)-dichloroacetamide as well as the novel compounds of formula I are capable of protecting cultures of sorghum and also maize from the phytotoxic action of herbicides of the chloroacetanilide class.

The haloacylamides of formula I are produced by a process, wherein an acylhalide of the formula II

    $R_1-CO-Hal$    (II)

wherein
Hal is chlorine or bromine and
$R_1$ has the meaning given under formula I,
is reacted in an inert organic solvent, in the presence of at least an equimolar amount of an acid-bridging agent, with an amine of the formula III

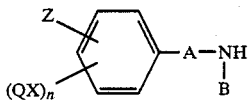

wherein A, B, n, Q, X and Z have the meaning given under formula I.

The reaction is suitably carried out at normal pressure in a solvent that is inert to the reactants. As solvents can be used e.g. aliphatic or aromatic hydrocarbons such as benzene, toluene, xylene, cyclohexan, petrol ethyl; halogenated hydrocarbons such as chlorobenzene, methylene chloride ethylenechloride, chloroform; ether and ether-like solvents like diethylether, di-isopropylether, t-butylmethylether, dimethoxyethan, dioxan, tetrahydrofuran, anisol; ketones like aceton, methylethylketon, esters like ethylacetate, butylacetate as well as mixtures of these solvents.

Acid-binding agents are especially tertiary amines such as trimethylamine, triethylamine, chinuclidine, 1,4-diazabicyclo(2,2,2)-octan, 1,5-Diazabicyclo(4.3.0)-non-5-en or 1.5-Diazabicyclo(5.4.0)-undecen-7-en. It is also possible to use inorganic bases, such as hydrides, sodium or calcium hydride, hydroxides like sodium or potassium hydride, carbonates such as sodium and potassium carbonate as well as hydrocarbonates such as sodium and potassium hydrogenocarbonate.

The starting materials of the formula II are known; the starting materials of the formula III are partially known, that is they can be produced according to known methods. Some of them are pharmaceuticals of the class of phenylalkylamines, alkoxy- or dialkoxy-phenylalkylamines or intermediate products for their preparation. The are use for influencing the vegetative nervous system.

In the published European Patent application EP-A 98 953, some of the following amines of formula III are listed:
2-(4-methoxyphenyl)-3-methyl-butylamine,
1,3-dimethyl-3-methoxyphenyl-butylamine,
1-methoxyphenyl-ethylamine,
3-methoxyphenyl-2-methyl-propylamine,
3-methoxyphenyl-pentylamine,
2-methoxyphenyl-1-methylethylamine,
2,3,4-trimethoxyphenylethylamine,
3,4-dimethoxybenzylamine,
N-(3,4,-dimethoxybenzyl)-N-isopropyl-amine,
N-(4-methoxybenzyl)-N-dimethoxymethyl-amine,
N-(4-methoxybenzyl)-N-ethyl-amine,
3-(4-methoxyphenyl)-3-methyl-propyl-amine,
N-(4-ethoxy-3-methoxybenzyl)-N-isopropyl-amine,
N-(3-chloro-4-methoxybenzyl)-N-isopropyl-amine,
N-(3,4-dimethoxybenzyl)-N-n-propyl-amine,
N-(3,4-dimethoxybenzyl)-N-(2-methoxyethyl)-amine,
N-(1,1-dimethyl-4-methoxybenzyl)-N-isopropyl-amine,
1,1-dimethyl-4-methoxy-benzyl-amine,
N-(4-trifluoromethylbenzyl)-N-isopropyl-amine,
N-(3,4-dimethoxybenzyl)-N-sec.-butyl-amine,
N-(3,4-dimethoxybenzyl)-N-allyl-amine,
N-(3,4-dimethoxy-1-methylbenzyl)-N-isopropyl-amine,
3,4-dimethoxy-1-methoxybenzyl-amine,
4-(1,3-dioxolan-2-ylmethoxy)-benzyl-amine,
N-(4-methoxybenzyl)-N-ethyl-amine,
N-(1-methyl-2-m-trifluormethoxyphenyl-ethyl)-N-ethyl-amine.

Other amines of the formula III are disclosed in J. Am. Chem. Soc. 95, 4438 (1973) and in Tetrahedron Letters 1978 5225:
3,4-dimethoxy-styrylamine,
N-(3,4-dimethoxybenzyl)-N′-ethoxycarbonyl-hydrazide,
N-(3,4-dimethoxybenzyl)-N-ethoxycarbonylmethyl-amine,
3-methoxy-4,5-methylendioxybenzyl-amine,
N-[2-(4-methoxyphenyl)-1-methyl]-N-methyl-amine,
N-(3,4-dimethoxybenzyl)-N-tetrahdrofurfuryl-amine,
1-cyano-4-methoxybenzyl-amine,
N-isopropyl-N-[2-(4-methoxyphenyl)-1-methyl]-amine,
4-methoxy-1-trifluoromethoxybenzyl-amine,
N-(3,4-dimethoxybenzyl)-N-(ααα-trifluoro-isopropyl)-amine,
N-(4-methoxy-1-methoxybenzyl)-N-isopropyl-amine,
N-(3,4-dimethoxybenzyl)-N-(1-cyanoethyl)-amine,
2-(3,4-dimethoxyphenyl)-2-methyl-propylamine,
2,2-difluoro-2-[4-trifluormethoxyphenyl)-ethyl-amine,
N-(3,4-dimethoxyphenylethyl)-N-isopropyl-amine,
N-(3,4-dimethoxybenzyl)-N-(α-chloroisopropyl)-amine,
N-(4-diethoxy-ethoxybenzyl)-N-n-propyl-amine,
N-(4-diethoxy-ethoxybenzyl)-N-isopropyl-amine,
N-(4-diethoxy-ethoxybenzyl)-N-allyl-amine, N-[3-(4-methoxyphenyl)-1-methyl-propyl]-N-isopropyl-amine, N-[3-(3,4-dimethoxyphenyl)-1-methylpropyl]-N-isopropyl-amine, N-[4-(1,3-dioxolan-2-ylmethoxy)-phenyl]-N-isopropyl-amine, 2-(3,4-dimethoxyphenyl-2-fluormethyliden-ethyl-amine.

Another process for the production of halogenoacyl-phenylalkylamines of the formula I, wherein $X_1$ has a different meaning than hydrogen consists in reacting a secondary amine of the formula IIIa

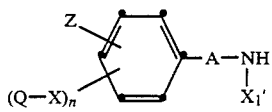

wherein A, n, Q, X and Z have the meaning given under Formula I while $X_1'$ represents a $C_1$-$C_4$-hydrocarbon radical that may be straight-chain or branched and which may be unsubstituted or substituted by alkoxy, halogen cyano or trifluoromethy; or $X_1'$ is cycloalkyl, dialkoxyalkyl, 1,3-dioxolan-2-ylalkyl, furylalkyl, tetrahydrofurylalkyl or a rest —NHCOOR, —CH$_2$COOR or —CH(CH$_3$)COOR wherein R has the meaning given under formula I, with choral or a chloral derivative whose oxo group is replaced by two oxy-addition-residues, in aqueous medium and/or in a polar organic solvent, in the presence of an acid-binding agent and a catalytic amount of an inorganic or organic cyamide.

The reaction scheme is as follows:

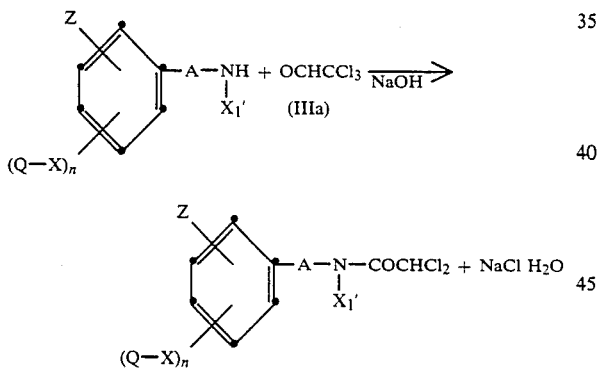

In this reaction chloral-hydrate can be used instead of chloral, or an excess of a secondary amine instead of sodium hydroxide may be used as well as e.g. an alkaline or alkaline-earth metal salt of a weak organic acid, such as e.g. sodium carbonate or calcium carbonate. The reaction is accelerated by the addition of an alkaline metal cyanide.

Different methods are necessary for the production of the amines of the formula III depending on their structure. If the bridging group A is methylene, the compounds are benzylamines, the production of which is sufficiently known. They can be produced e.g. by hydrogenating of Benzonitriles which are substituted in the phenyl ring according to the meaning of n, P, X and Z.

By catalytic reduction of acetophenoximes, which are approximately substituted in the phenyl ring α-methyl-benzylamines can be obtained, and by catalytic reduction of the corresponding α, α, α-trifluoroacetophenoximes one obtaines benzylamines which are substituted in the α-position by the trifluoromethyl group.

Further benzylamines, which are substituted in the α-position can be obtained by adding an appropriately substituted benzoyl derivative to an amine and heating the addition product in the presence of formic acid, formamide or ammoniumformiate in the presence of a catalytic amount of a Lewis acid (c. f. R. Leuckart, Ber. 22, 1409 and 1851 (1889).

By the degradation of α,α-phenylacetic acid amides, which are appropriately substituted in the phenyl ring by means of an alkalihypogenit in aqueous medium at about 70°, the phenylacetic acid amine can be decarboxylated to the corresponding benzylamine, (cf. A. W. Hoffman, Ber. 18, 2734 (1885))

By hydrating benzylcyamides, which are substituted in the phenyl ring, according to the meanings of n, P, X and Z, the corresponding phenylethylamines can be produced. Starting e.g. from 3-Trifluoromethoxybenzylchloride, (known from German Offenlegungsschrift 3 228 728) and an alkaline cyanide, it is possible to produce 3-Trifluoromethoxyphenylethylamine, If the benzylcyanide is substituted in the α-position by one or two alkyl radicals, the correspondingly substituted 2-acyl-2-alkylethylamine and 2-aryl-2,2-dialkylethylamine are obtained as shown by the following reaction scheme:

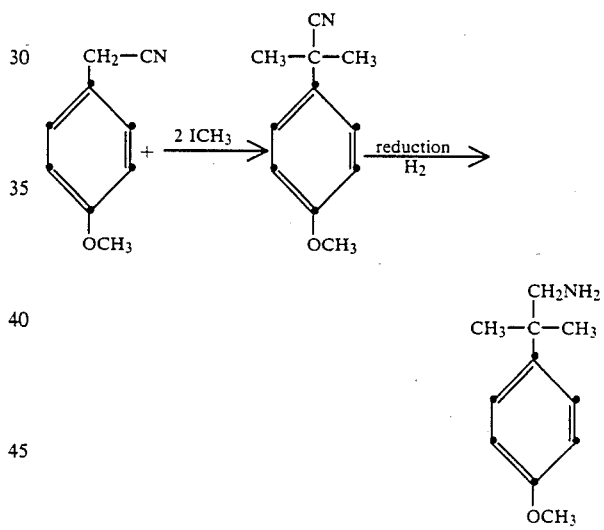

It is also possible to add halogenoacyl groups to secondary amines. The secondary amines can easily be prepared according to known methods by reaction of an appropriately substituted aromatic aldehyde with a primary amine and hydrogenation of the addition product. By condensing 3,4-dimethoxybenzaldehyde with 1-methyl-2,2,2-trifluoroethylamine and hydrogenation of the condensate, N-(3,4-dimethoxybenzyl)-N-(1-methyl-2,2,2-trifluoroethyl)-amine is obtained according to the following reaction scheme:

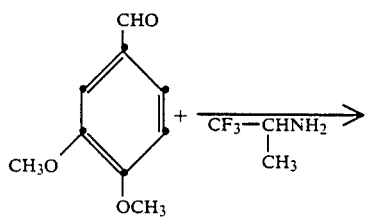

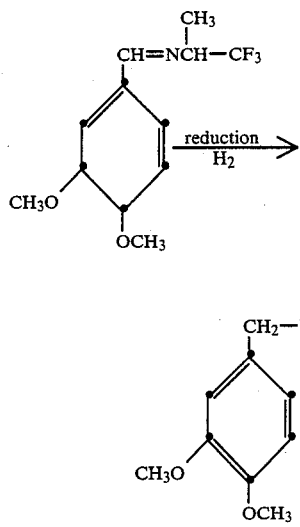

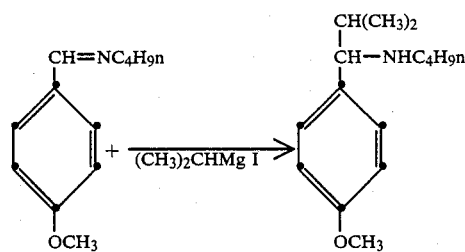

(c.f. the German Offenlegungsschrift DE-OS 3 218 201)

Schiff'-bases are convenient starting material for the production of further secondary amines, Thus e.g. starting from 4-methoxybenzylidene-butylamine and isopropylmagnesiumiodide on obtaines N-(4-methoxybenzyl)-N-isopropyl-N-butylamine according to the reaction scheme:

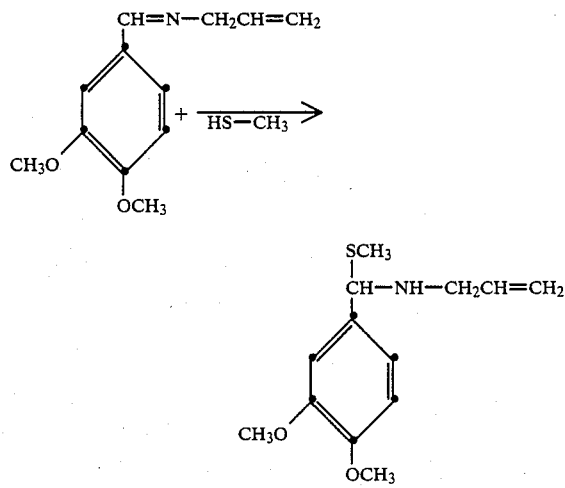

Another example for the production of amines of the formula III is e.g. the addition of allylmercaptan to a Schiff'-base, such as the addition of 3,4-dimethoxybenzyliden-allylamine and methylmercaptan according to the reaction scheme:

(c.f. the published European patent application EP-A 93 610)

In the same manner can be obtained by reaction of Schiff'-bases with trichloroacetic acid according to the following reaction scheme e.g. N-(α-trichloromethyl-benzyl)-N-isopropylamine

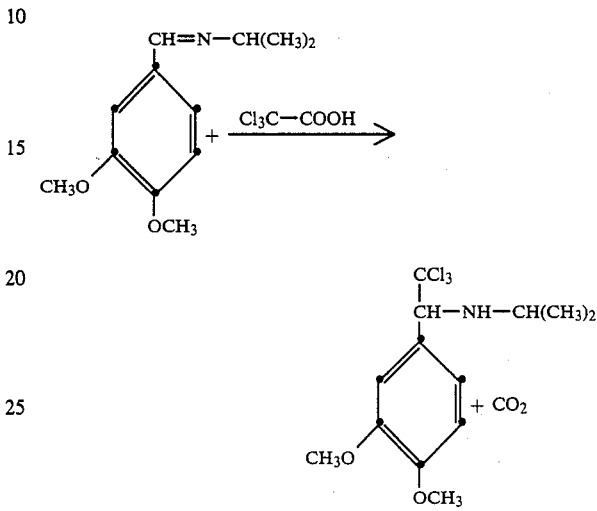

Depending on the purpose for which it is used, a counter-agent or antidote of the formula I can be employed for pretreating the seed of the cultivated plant (dressing the seed or cuttings), or can be applied to the soil before or after sowing. It can, however, also be applied on its own or together with the herbicide before or after the emergence of the plants. In principle, therefore, the treatment of the plant or the seed with the antidote can be effected independently of the time when the phytotoxic chemical is applied. The treatment of the plant can, however, also be effected by the simultaneous application of the phytotoxic chemical and the counter-agent (tank mixture). Pre-emergence treatment includes both the treatment of the cultivated area before sowing (ppi=pre plant incorporation and the treatment of the cultivated areas which have been sown, but are not yet covered with green vegetation.

The amounts of the counter-agent applied, in relation to the herbicide, depend largely on the mode of application. In a field treatment, in which the herbicide and the counteragent are either applied simultaneously (tank mixture) or are applied separately, the ratio of the amount of counter-agent to that of herbicide is within the range from 1:100 to 5:1. As a rule, the full protective action is achieved at a ratio of counter-agent to herbicide of 1:5 to 1:50. In seed dressing and similar selective protective measures, however, much smaller amounts of counter-agent are required in comparison with the amounts of herbicide used in later per hectare of cultivated area. In general, 0.1–10 g of counter-agent per kg of seed are required in seed dressing. As a rule, the full protective action is achieved at a level as low as 0.1–5 g of counter-agent per kg of seed. If the counter-agent is to be applied by seed soaking shortly before sowing, it is advantageous to use solutions of the counteragent containing the active compound in a concentration of 1–10,000 ppm. As a rule, the full protective action is achieved using concentrations of 100–1,000 ppm of the counter-agent.

As a rule, there is a fairly long period of time between protective measures, such as seed dressing and the treatment of cuttings with a counter-agent of the formula I, and the possible later field treatment with agricultural chemicals. In agriculture, horticulture and forestry, pretreated seed and plant material can later come into contact with various chemicals. The invention also relates, therefore, to protective compositions, for cultivated plants, containing, as the active substance, the counter-agent of the formula I together with customary carriers. Compositions of this type can, if desired, additionally contain the agricultural chemicals exerting the effect against which the cultivated plant is to be protected.

Within the scope of the present invention, cultivated plants are to be considered as any plants which produce, in any form, harvested materials, such as seeds, roots, stalks, tubers, leaves, flowers and contained substances, such as oils, sugar, starch, protein etc., and which are cultivated for this purpose. These plants include, for example, all species of cereals, such as wheat, rye, barley and oats as well as, in particular, rice, cultivated millet, maize, cotton, sugar beet, sugar cane, soya, beans and peas.

The counter-agent can be employed in all cases where a cultivated plant of the type mentioned above is to be protected against the harmful action of an agricultural chemical. Possible agricultural chemicals in this sense are primarily herbicides of a very wide variety of classes of substances, but particularly halogenoacetanilides and thiocarbamates.

Halogenoacetanilides exerting a harmful action against cultivated plants which can be counteracted by means of the active substance of the formula I are already known in large numbers. Halogenoacetanilides of this type can be described by the following general formula IV.

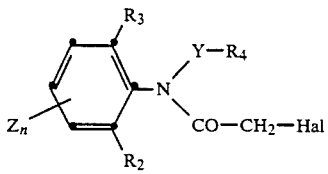

In this formula, Hal is halogen, in particular chlorine or bromine, $R_2$ and $R_3$ independently of one another are each hydrogen, halogen or lower alkyl, alkoxy, alkylthio, halogenoalkyl, alkoxyalkyl or alkylthioalkyl, Z is hydrogen, halogen or lower alkyl, alkoxy, alkylthio, halogenoalkyl, alkoxyalkyl or alkylthioalkyl, the above-mentioned radicals Z being preferably in the 3-position in relation to the nitrogen atom, n is 0 to 3, Y is alkylene, especially methylene or 1,1-ethylene and 1,2-ethylene, it being possible for 1,2-ethylene to be substituted by 1- 2 lower alkyl groups, and $R_4$ is lower alkoxy, hydroxycarbonyl alkoxycarbonyl, carbamoyl, N-alkylcarbamoyl, N,N-dialkylcarbamoyl, cyano, a substituted or unsubstituted, nitrogen-containing, heterocyclic radical, alkanoyl, substituted or unsubstituted benzoyl or substituted or unsubstituted 1,3,4-oxadiazol-2-yl, 1,3,4-thiadiazol-2-yl, 1,3,4-triazol-3-yl or 1,3,4-triazol-l-yl.

The following may be mentioned as examples of individual representatives of such halogenoacetanilides: N-ethoxymethyl-N-chloroacetyl-2ethyl-6-methylaniline, N-chloroacetyl-N-methoxymethyl-2,6-diethylaniline, N-chloroacetyl-N-(2-methoxyethyl)-2,6-dimethylaniline, N-(2-allyloxyethyl)-N-chloroacetyl-2,6-dimethylaniline, N-chloroacetyl-N-(2-n-propoxyethyl)-2,6-dimethylaniline, N-chloroacetyl-N-(2-iso-propoxyethyl)-2,6-dimethylaniline, N-chloroacetyl-N-(2-methoxyethyl)-2-ethyl-6-methylaniline, N-chloroacetyl-N-(methoxyethyl)-2,6-diethylaniline, N-(2-ethoxyethyl)-N-chloroacetyl-2-ethyl-6-methylaniline, N-chloroacetyl-N-(2-methoxy-1-methylethyl)-2-methylaniline, N-chloroacetyl-N-(2-methoxy-1-methylethyl)-2,6-dimethylaniline, N-chloroacetyl-N-(2-methoxy-1-methylethyl)-2,6-diethylaniline, N-chloroacetyl-N-(2-methoxy-1-methylethyl)-2-ethyl-6-methylaniline, N-(2-ethoxyethyl)-N-chloroacetyl-2,6-diethylaniline, N-chloroacetyl-N-(2-n-propoxyethyl)-2-ethyl-6-methylaniline, N-chloroacetyl-N-(2-n-propoxyethyl)-2,6-diethylaniline, N-chloroacetyl-N-(2-isopropoxyethyl)-2-ethyl-6-methylaniline, N-ethoxycarbonylmethyl-N-chloroacetyl-2,6-dimethylaniline, N-ethoxycarbonylmethyl-N-chloroacetyl-2,6-diethylaniline, N-chloroacetyl-N-methoxycarbonylmethyl-2,6-dimethylaniline, N-chloroacetyl-N-(2,2-diethoxyethyl)-2,6-dimethylaniline, N-chloroacetyl-N-(2-methoxy-1-methylethyl)-2,3-dimethylaniline, N-(2-ethoxyethyl)-N-chloroacetyl-2-methylaniline, N-chloroacetyl-N-(2-methoxyethyl)-2-methylaniline, N-chloroacetyl-N-(2-methoxy-2-methylethyl)-2,6-dimethylaniline, N-(2-ethoxy-2-methylethyl)-N-chloroacetyl-2-ethyl-6-methylaniline, N-chloroacetyl-N-(1-ethyl-2-methoxyethyl)-2,6-dimethylaniline, N-chloroacetyl-N-(2-methoxyethyl)-2-methoxy-6-methylaniline, N-n-butoxymethyl-N-chloroacetyl-2-tert.-butylaniline, N-(2-ethoxyethyl-1-methylethyl)-2,6-dimethylaniline, N-chloroacetyl-N-(2-methoxyethyl)-2-chloro-6-methylaniline, N-(2-ethoxyethyl)-N-chloroacetyl-2-chloro-6-methylaniline, N-(2-ethoxyethyl)-N-chloroacetyl-2,3,6-trimethylaniline, N-chloroacetyl-l-(2-methoxyethyl)-2,3,6-trimethylaniline, N-chloroacetyl-N-cyanomethyl-2,6-dimethylaniline, N-but-3-in-l-yl-N-chloroacetylaniline, N-chloroacetyl-N-propargyl-2-ethyl-6-methylaniline, N-chloroacetyl-N-(1,3-dioxolan-2-ylmethyl)-2,6-dimethyl aniline, N-chloroacetyl-N-(1,3-dioxolan-2-ylmethyl)-2-ethyl-6-methylaniline, N-chloroacetyl-N-(1,3-dioxan-2-ylmethyl)-2-ethyl-6-methylaniline, N-chloroacetyl-N-(2-furanylmethyl)-2,6-dimethylaniline, N-chloroacetyl-N-(2-furanylmethyl)-2ethyl-6-methylaniline, N-chloroacetyl-N-(2-tetrahydrofuranylmethyl)-2,6-dimethylaniline, N-chloroacetyl-N-(N-propargylcarbamoylmethyl)-2,6-dimethylaniline, N-chloroacetyl-N-(N,N-dimethylcarbamoylmethyl)-2,6-dimethylaniline, N-(n-butoxymethyl)-N-chloroacetyl-2,6-diethylaniline, N-(2-n-butoxyethyl)-N-chloroacetyl-2,6-diethylaniline, N-chloroacetyl-N-(2-methoxy-1,2-dimethylethyl)-2,6-dimethylaniline, N-chloroacetyl-N-isopropyl-2,3-dimethylaniline, N-chloroacetyl-N-isopropyl-2-chloroaniline, N-chloroacetyl-N-(1H-pyrazol-1-ylmethyl)-2,6-dimethylaniline, N-chloroacetyl-N-(1H-pyrazol-1-ylmethyl)-2-ethyl-6-methylaniline, N-chloroacetyl-N-(1H-1,2,4-triazol-1-ylmethyl)-2,6-dimethylaniline, N-chloroacetyl-N-(1H-1,2,4-triazol-1-ylmethyl)-2,6-diethylaniline, N-benzoylmethyl-N-chloroacetyl-2,6-dimethylaniline, N-benzoylmethyl-N-chloroacetyl-2-ethyl-6-methylaniline, N-chloroacetyl-N-(5-methyl-1,3,4-oxadiazol-2-yl)-2,6-diethylaniline, N-chloroacetyl-N-(5-methyl-1,3,4-oxadiazol-2-yl)-2-ethyl-6-methylaniline, N-chloroacetyl-N-(5-methyl-1,3,4-oxadiazol-2-yl)-2-tert.-butylaniline, N-chloroacetyl-N-(4-chlorobenzoylmethyl)-2,6-dimethylaniline and N-chloroacetyl-N-(1-methyl-5-methylthio-1,3,4-triazol-2-ylmethyl)-2,6-diethylaniline.

Further halogenoacetanilides exerting a harmful action, on cultivated plants, which can be counteracted by the novel active substance of the formula I are listed in R. Wegler, Chemie der Pflanzenschutz- und Schädlingsbekämpfungsmittel ("The Chemistry of Plant Protection Compositions and Pest Control Compositions"), volume 8, pages 90–93 and pages 322–327.

Unless it is used to dress seed, the amount of the counter-agent applied varies between about 0.01 and about 5 parts by weight per part by weight of herbicide. The most suitable ratio based on optimum action on the particular cultivated plant is determined on a case by case basis, i.e. depending on the type of herbicide used.

The invention also relates to a process for selectively controlling weeds in crops of cultivated plants, the crops of cultivated plants, parts of the cultivated plants or areas cultivated for cultivated plants being treated with a herbicide and the compound of the formula I or a composition containing this combination. The compositions containing the herbicide/antidote combination also form a part of the present invention.

The weeds to be controlled can be either monocotyledonous or dicotyledonous weeds.

Various methods and techniques are suitable for using the compound of the formula I or compositions containing it in order to protect cultivated plants against the harmful effects of agricultural chemicals, for example the following methods and techniques:

(i) Seed dressing (a) Dressing the seed with an active substance, formulated as a wettable powder, by shaking in a vessel until uniform distribution over the surface of the seed is achieved (dry dressing). In this procedure, about 10 to 500 g of active substance of the formula I (40 g to 2 kg of wettable powder) are used per 100 kg of seed.

(b) Dressing the seed with an emulsion concentrate of the active substance of the formula I by method (a) (wet dressing).

(c) Dressing by immersing the seed in a liquor containing 50–3,200 ppm of an active substance of the formula I for 1 to 72 hours and, if desired, subsequently drying the seed (immersion dressing).

Dressing the seed or treating the sprouted seedling are, of course, the preferred methods of application, because the treatment with active substance is directed entirely towards the target crop. As a rule, 10 g to 500 g, preferably 50 to 250 g, of active substance are used per 100 kg of seed, and, depending on the method employed, which also enables other active substances or micro-nutrients to be added, it is possible to exceed or to use less than the limiting concentrations indicated (repeat dressing).

(ii) Application from a tank mixture

A liquid formulation of a mixture of counter-agent and herbicide (ratio of the one to the other between 10:1 and 1:30) is used, the application rate of herbicide being 0.1 to 10 kg per hectare. A tank mixture of this type is preferably applied before or immediately after sowing or is worked 5 to 10 cm deep into the soil before sowing.

(iii) Application to the seed furrow

The counter-agent is introduced, in the form of an emulsion concentrate, wettable powder or granules, into the open, sown seed furrow and then, after the seed furrow has been covered in a normal manner, the herbicide is applied by the pre-emergence process.

(iv) Controlled release of active substance

A solution of the active substance is absorbed onto mineral granular carriers or polymerised granules (urea/formaldehyde) and is allowed to dry. If desired, it is possible to apply a coating (coated granules) which enables the active substance to be released in a metered manner over a specific period of time.

The compound of the formula I is employed in an unaltered form or, preferably, together with the adjuncts conventionally used in the art of formulation and are, therefore, processed in a known manner to give, for example, emulsion concentrates, solutions which can be atomised or diluted without further treatment, dilute emulsions, wettable powders, soluble powders, dusts, granules and also encapsulations in, for example, polymeric substances. The application processes, such as atomizing, nebulizing, dusting, sprinkling or watering, are selected to suit the intended aims and the given circumstances, as is also the type of composition.

The formulations, i.e. the compositions, preparations or combinations containing the active substance of the formula I and, if appropriate, a solid or liquid adjuvant, are prepared in a known manner, for example by intimately mixing and/or grinding the active substances with extenders, for example solvents, solid carriers and, if appropriate, surface-active compounds (surfactants).

The following can be suitable as solvents: aromatic hydrocarbons, preferably the fractions from $C_8$ to $C_{12}$, for example mixed xylenes or substituted naphthalenes, phthalic acid esters, such as dibutyl or dioctyl phthalate, aliphatic hydrocarbons, such as cyclohexane or paraffins, alcohols and glycols and also ethers and esters thereof, such as ethanol, ethylene glycol or ethylene glycol monomethyl or monoethyl ether, ketones, such as cyclohexanone, strongly polar solvents, such as N-methyl-2-pyrrolidone, dimethyl sulfoxide or dimethylformamide, and epoxidised or unepoxidised vegetable oils, such as epoxidised coconut oil or soya oil; or water.

The solid carriers used, for example for dusts and dispersible powders, are, as a rule, natural ground minerals, such as calcite, talc, kaolin, montmorillonite or attapulgite. It is also possible to add highly disperse silica or highly disperse absorbent polymers in order to improve the physical properties. Suitable particulate, adsorptive granular carriers are porous types, for example pumice stone, broken brick, sepiolite or bentonite, while examples of suitable non-sorptive carriers are calcite or sand. In addition, it is possible to use a large number of pregranulated materials of an inorganic or organic nature, such as, in particular, dolomite or comminuted plant residues.

Suitable surface-active compounds are nonionic, cationic and/or anionic surfactants having good emulsifying, dispersive and wetting properties. Surfactants are also to be understood as meaning mixtures of surfactants.

Suitable anionic surfactants can be so-called water-soluble soaps as well as water-soluble synthetic surface-active compounds.

Examples of soaps are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids, which can be obtained, for example, from coconut oil or tallow oil. Furthermore, mention should also be made of the salts of fatty acid methyltaurides.

More frequently, however, so-called synthetic surfactants are used, in particular fatty sulfonates, fatty sulfates, sulfonated benzimidazole derivatives or alkylarylsulfonates.

The fatty sulfonates or sulfates are, as a rule, in the form of alkali metal salts, alkaline earth metal salts or substituted or unsubstituted ammonium salts and contain an alkyl radical having 8 to 22 C atoms, in which connection alkyl also includes the alkyl moiety of acyl radicals, for example the Na or Ca salt of ligninsulfonic acid, of dodecylsulfuric acid ester or of a mixture of fatty alcohol sulfates prepared from natural fatty acids. Included under this heading are also the salts of the sulfuric acid esters and sulfonic acids or fatty alcohol-/ethylene oxide adducts. The sulfonated benzimidazole derivatives preferably contain 2 sulfonic acid groups and a fatty acid radical having 8–22 C atoms. Examples of alkylarylsulfonates are the Na, Ca or triethanolamine salts of dodecylbenzenesulfonic acid, of dibutylnaphthalenesulfonic acid or of a naphthalenesulfonic acid/-formaldehyde condensation product.

Furthermore, corresponding phosphates, for example salts of the phosphoric acid ester of a p-nonylphenol/-(4–14)-ethylene oxide adduct, or phospholipids are also suitable.

Suitable nonionic surfactants are primarily polyglycol ether derivatives of aliphatic or cycloaliphatic alcohols, saturated or unsaturated fatty acids and alkylphenols; these derivatives can contain 3 to 30 glycol ether groups and 8 to 20 carbon atoms in the (aliphatic) hydrocarbon radical and 6 to 18 carbon atoms in the alkyl radical of the alkylphenols.

Further suitable nonionic surfactants are the water-soluble adducts, containing 20 to 250 ethylene glycol ether groups and 10 to 1,00 propylene glycol ether groups, of polyethylene oxide with polypropylene glycol, ethylenediaminiopolypropylene glycol and an alkylpolypropylene glycol having 1 to 10 carbon atoms in the alkyl chain. The said compounds usually contain 1 to 5 ethylene glycol units per unit of propylene glycol.

Examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Furthermore, fatty acid esters of polyoxyethylenesorbitan, such as polyoxyethylenesorbitan trioleate, are also suitable.

The cationic surfactants are, in particular, quaternary ammonium salts which contain, as N-substituents, at least one alkyl radical having 8 to 22 C atoms and, as further substituents, lower, halogenated or unhalogenated alkyl radicals, benzyl radicals or lower hydroxyalkyl radicals. The salts are preferably in the form of halides, methylsulfates or ethylsulfates, for example stearyltrimethylammoniumchloride or benzyldi-(2-chloroethyl)ethylammonium bromide.

The surfactants which are conventional in the art of formulation are described, inter alia, in the following publications: "McCutcheon's Detergents and Emulsifiers Annual", MC Publishing Corp., Ridgewood, New Jersey, 1981; H. Stache, "Tensid-Taschenbuch" ("Surfactants Manual"), 2nd edition, C. Hanser Verlag, Munich, Vienna, 1981; M. and J. Ash, "Encyclopedia of Surfactants", vol. I–III, Chemical Publishing Co., New York, 1980–1981.

The agrochemical preparations contain, as a rule, 0.1 to 95%, in particular 0.1 to 80%, of active substance, 1 to 99.9% of a solid or liquid adjuvant and 0 to 25%, in particular 0.1 to 25%, of a surfactant.

In particular, the composition of preferred formulations is as follows: (%=percent by weight)

| Emulsifiable concentrates | |
|---|---|
| Active substance: | 1 to 20%, preferably 5 to 10% |
| Surface-active agent: | 5 to 30%, preferably 10 to 20% |
| Liquid carrier: | 50 to 94%, preferably 70 to 85% |
| Dusts: | |
| Active substance: | 0.1 to 10%, preferably 0.1 to 1% |
| Solid carrier: | 99.9 to 90% preferably 99,9 to 99% |
| Suspension concentrates: | |
| Active substance: | 5 to 75%, preferably 10 to 50% |
| Water: | 94 to 25%, preferably 90 to 30% |
| Surface active agent: | 1 to 40%, preferably 2 to 30% |
| Wettable powders | |
| Active substance: | 0.5 to 90%, preferably 1 to 80% |
| Surface-active agent: | 0.5 to 20%, preferably 1 to 15% |
| Solid carrier: | 5 to 95%, preferably 15 to 90% |
| Granules | |
| Active substance: | 0.5 to 30%, preferably 3 to 15% |
| Solid carrier: | 99.5 to 70%, preferably 97 to 85%. |

Whereas concentrated compositions are more likely to be preferred as commercial products, the final consumer as a rule uses dilute compositions. The application forms can be diluted down to 0,001% of active substance. The application rates are, as a rule, 0.01 to 10 kg of active substance per hectare, preferably 0.025 to 5 kg of active substance per hectare.

The compositions can also contain further adjuvants, such as stabilisers, anti-foaming agents viscosity regulators, binders, tackifiers and fertilizers or other active substances for achieving special effects.

In the following examples the temperatures are quoted in degrees centigrade, °C., and the pressures in millibar, mb.

EXAMPLE 1:

Process for the production of N-(3,4-dimethoxybenzyl)-N-isopropyl-dichloroacetamide

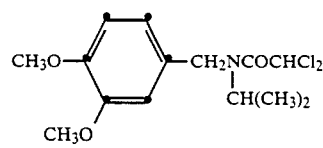

A mixture of 126 g N-(3,4-dimethoxybenzyl)-N-isopropyl amine (prepared by condensing 3,4-dimethoxybenzaldehyde and isopropylamine and hydrogenating the conversation product b.p. 77.5°–77.8°/0.03 mbar) and 250 ml of toluene is stirred in a 750 ml 4-neckflask until the amine is dissolved. Then 120 g of 20% sodium hydroxide is added thereto and the reaction-mixture is cooled in a CO₂/alcohol bath to a temperature of −10°/−15°. A mixture of 89 g of dichloroacetic acid chloride in 100 ml of toluene is then added dropwise while stirring to the cold reaction mixture. A white precipitate forms immediately. When everything is added, what takes about 1½hours, the cooling bath is removed and the reaction mixtured is stirred until room temperature has been reached. Then it is poured into an ice-water mixture. The phases are separated and the water-phase is extracted with toluene. The organic layer is then washed twice with 1N hydrochloric acid and twice with water, dried and concentrated. There remain 176 g (91.7% of the theory) or a clear sticky oil with a refraction index of $n_D^{22}$ 1.5495 which eventually crystallizes m.p. 69°–72°.

EXAMPLE 2:

Process for the production of N-(4-trifluoromethylbenzyl)-N-isopropyl-dichloroacetamide

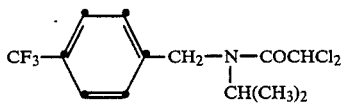

A solution of 21.7 g of N-(4-trifluoromethylbenzyl)-N-isopropyl-amine is added while stirring in a 4 neck-flask with 20 ml of 20% sodium-hydroxide solution. The reaction-mixture is then cooled while stirring in an alcohol/CO₂-bath to a temperature of from −10° to −5° whereupon 14.7 g of dichloroacetyl chloride is added slowly, dropwise thereto. After about ½ hour, when everything is added, the cooling-bath is removed and the reaction mixture is stirred for 2 hours until it reaches room temperature. It is then poured into ice-/water and the organic material is extracted with toluene. The toluene-phases are collected washed first with diluted sodium hydroxide, then with diluted hydrochloric acid and eventually twice with water, dried over sodium sulfate and concentrated in a rotatory evaporator. A clear oil is thus obtained, which becomes solid after a while. The solid mass is then triturated with hexane and filtered to yield 21.7 g of crystalline N-(4-trifluoromethylbenzyl)-N-isopropyl-dichloroacetamide, melting at 92° to 93°.

EXAMPLE 3:

Process for the production of N-(3,4-dimethoxyphenylethyl)-N-isopropyl-dichloroacetamide

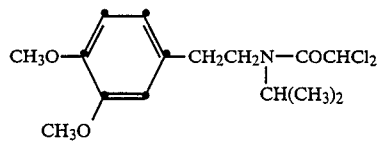

In a sulfuration-flask, there is added while stirring 20 ml of 20% aqueous sodium hydroxide to 22,3 g of N-(3,4-dimethoxyphenylethyl)-N-isopropyl amine. The reaction mixture is then cooled in CO₂ alcohol-cooling-bath to a temperature of −10° to −15°, to which is then added dropwise, while stirring a solution of 14.7 g of dichloroacetylchloride in 10 ml toluene. After everything has been added, the cooling-bath is removed and the reaction mixture is stirred for another 2 hours until it reaches room-temperature. It is then poured into an ice/water mixture and the organic material is extracted with toluene. The toluene extracts are washed once with diluted sodium hydroxide and with diluted hydrochloric acid and twice with water dried over sodium sulfate and concentrated in an rotatory evaporator. The title product is thus obtained as viscous oil in a yield of 28.4 g.

In a manner analogous to these examples, the following compounds were produced:

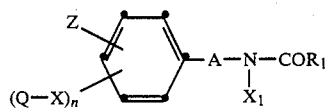

| No | Z | (P—Q)$_n$ | A | B | R$_1$ | phys. data |
|---|---|---|---|---|---|---|
| 1 | H | 3,4(CH₃O)₂ | CH₂ | CH(CH₃)₂ | CHCl₂ | mp. 69–72° example 1 |
| 2 | H | 4-CF₃ | CH₂ | CH(CH₃)₂ | CHCl₂ | mp. 82–83° example 2 |
| 3 | H | 3,4(CH₃O)₂ | C₂H₄ | CH(CH₃)₂ | CHCl₂ | viscous oil example 3 |
| 4 | H | 4-CH₃O | CH₂ | H | CHCl₂ | mp. 105–107° |
| 5 | H | 4-CH₃O | CH₂ | CH(CH₃)₂ | CHCl₂ | b.p. 151–155° /0.08 mbar |
| 6 | H | 4-(CH₃)₂CHO | CH₂ | H | CHCl₂ | mp. 80–82° |
| 7 | H | 4-(CH₃)₂CHO | CH₂ | H | CH₂Cl | mp. 67–68° |
| 8 | H | 4-(1,3-di-oxolan-2-yl-methoxy)- | CH₂ | H | CHCl₂ | mp. 145–148° |
| 9 | H | 3,4(CH₃O)₂ | CH₂ | H | CH₂Cl | mp. 117–118° |
| 10 | H | 3,4(CH₃O)₂ | CH₂ | H | CHCl₂ | mp. 110–112° |
| 11 | H | 4-CH₃O | CH(CH₃) | H | CH₂Cl | mp. 55–58° |
| 12 | H | 4-CH₃O | CH₂CH(CH₃) | H | CH₂Cl | mp. 82–84° |
| 13 | H | 4-CH₃O | CH₂ | 1,4-di-oxolan-2-yl-methyl | CHCl₂ | oil |
| 14 | H | 4-CH₃O | CH₂ | C₂H₅ | CHCl₂ | oil |
| 15 | H | 3,4(CH₃O)₂ | CH₂ | CH(CH₃)₂ | CHCl—CH₃ | oil |
| 16 | H | 3,4(CH₃O)₂ | CH₂CH₂ | CH(CH₃)₂ | CH₂Cl | oil |
| 17 | H | 3,4(CH₃O)₂ | CH₂ | CH(CH₃)C₂H₅ | CHCl₂ | oil |
| 18 | H | 3,4(CH₃O)₂ | CH₂ | C₃H₇—n | CHCl₂ | oil |
| 19 | H | 3,4(CH₃O)₂ | CH₂ | C₂H₄OCH₃ | CHCl₂ | mp. 80–81° |
| 20 | H | 3,4(CH₃O)₂ | CH₂ | CH₂CH=CH₂ | CH₂Cl | |
| 21 | H | 3,4(CH₃O)₂ | CH₂ | CH₂CH=CH₂ | CHCl₂ | |
| 22 | H | 3,4(CH₃O)₂ | CH₂CH₂ | CH₂CH=CH₂ | CH₂Cl | |

-continued

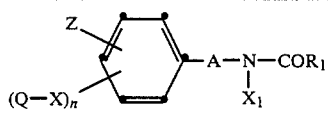

| No | Z | (P—Q)$_n$ | A | B | R$_1$ | phys. data |
|----|---|-----------|---|---|-------|------------|
| 23 | H | 3,4(CH$_3$O)$_2$ | CH$_2$CH$_2$ | CH$_2$CH=CH$_2$ | CHCl$_2$ | |
| 24 | H | 3,4(CH$_3$O)$_2$ | CH(CH$_3$) | CH(CH$_3$)$_2$ | CH$_2$Cl | |
| 25 | H | 3,4(CH$_3$O)$_2$ | CH(CH$_3$) | CH(CH$_3$)$_2$ | CHCl$_2$ | oil |
| 26 | H | 4-CF$_3$ | CH$_2$ | H | CH$_2$Cl | mp. 95-97° |
| 27 | H | 4-CF$_3$ | CH$_2$ | CH(CH$_3$)$_2$ | CH$_2$Cl | oil |
| 28 | H | 3-CF$_3$ | CH$_2$ | H | CH$_2$Cl | |
| 29 | H | 3-CF$_3$ | CH$_2$ | H | CHCl$_2$ | |
| 30 | H | 3-CF$_3$ | CH$_2$ | CH(CH$_3$)$_2$ | CH$_2$Cl | |
| 31 | H | 3-CF$_3$ | CH$_2$ | CH(CH$_3$)$_2$ | CHCl$_2$ | |
| 32 | H | 3,4(CH$_3$O)$_2$ | CH$_2$ | NH—COOC$_2$H$_5$ | CHCl$_2$ | mp. 80-83° |
| 33 | H | 3,4(CH$_3$O)$_2$ | CH$_2$ | tetrahydro-furan-2-yl | CHCl$_2$ | mp. 84-86° |
| 34 | H | 4-[1,4-di-oxolan-2-yl-methyl | CH$_2$ | CH(CH$_3$)$_2$ | CHCl$_2$ | |
| 35 | 3-Cl | 4-CH$_3$O | CH$_2$ | CH(CH$_3$)$_2$ | CHCl$_2$ | |
| 36 | H | 4-(CH$_3$O)$_2$CHCH$_2$O— | CH$_2$ | CH(CH$_3$)$_2$ | CHCl$_2$ | |
| 37 | H | 3,4(CH$_3$O)$_2$ | CH$_2$ | C$_2$H$_3$(OC$_2$H$_5$)$_2$ | CHCl$_2$ | |
| 38 | H | 4-CH$_3$O | CH$_2$ | tetrahydro furan-2-yl | CHCl$_2$ | |
| 39 | H | N≡C—CH$_2$O | CH$_2$ | CH(CH$_3$)$_2$ | CHCl$_2$ | |
| 40 | H | 4-CH$_3$O | CH(CCl$_3$) | CH(CH$_3$)$_2$ | CHCl$_2$ | |
| 41 | H | 3,4-(CH$_3$O)$_2$ | CH(SCH$_3$) | CH(CH$_3$)$_2$ | CHCl$_2$ | |
| 42 | H | 3,4(CH$_3$O)$_2$ | C(CH$_3$)$_2$—CH$_2$ | CH(CH$_3$)$_2$ | CHCl$_2$ | |
| 43 | H | 3,4(CH$_3$O)$_2$ | CH$_2$—CH(CH$_3$) | CH(CH$_3$)$_2$ | CHCl$_2$ | |
| 44 | H | 3-CH$_3$O | CH$_2$ | CH(CH$_3$)$_2$ | CHCl$_2$ | oil |
| 45 | H | 2-CH$_3$O | CH$_2$ | CH(CH$_3$)$_2$ | CHCl$_2$ | mp. 81-82° |
| 46 | H | 2,4(CH$_3$O) | CH$_2$ | CH(CH$_3$)$_2$ | CHCl$_2$ | mp. 117-119° |
| 47 | H⁻ | 2,5(CH$_3$O) | CH$_2$ | CH(CH$_3$)$_2$ | CHCl$_2$ | oil |
| 48 | H | 2,3(CH$_3$O) | CH$_2$ | CH(CH$_3$)$_2$ | CHCl$_2$ | oil |
| 49 | H | 3,4(CH$_3$O) | CH$_2$ | CH$_2$CH(CH$_3$)$_2$ | CHCl$_2$ | oil |
| 50 | H | 4-CH$_3$O | CH$_2$ | CH$_2$CH(OCH$_3$)$_2$ | CHCl$_2$ | oil |
| 51 | H | 3,4,5(CH$_3$O)$_3$ | CH$_2$ | CH(CH$_3$)$_2$ | CHCl$_2$ | oil |
| 52 | H | 4-CH$_3$O | CH$_2$ | CH(CH$_3$)$_2$ | CHCl$_2$ | oil |
| 53 | H | 2,5(CH$_3$O)$_2$ | CH$_2$ | CH$_2$CH(CH$_3$) | CHCl$_2$ | |
| 54 | 4-CH$_3$ | 2,5(CH$_3$O)$_2$ | CH$_2$CH(CH$_3$) | H | CHCl$_2$ | |
| 55 | 4-CH(CH$_3$)$_2$ | 2,5(CH$_3$O)$_2$ | CH$_2$CH(CH$_3$) | H | CHCl$_2$ | |
| 56 | H | 3,4(CH$_3$O)$_2$ | C(=CF)CH$_2$ | H | CHCl$_2$ | |
| 57 | H | 3,4,5(CH$_3$O)$_3$ | CH$_2$CH$_2$ | CH$_2$CH(CH$_3$)$_2$ | CHCl$_2$ | |
| 58 | 3-CH$_3$O | 4-C$_2$H$_5$O | CH$_2$ | CH(CH$_3$)$_2$ | CHCl$_2$ | oil |
| 59 | H | 4-CH$_3$O | CH$_2$CH(CH$_3$) | CH(CH$_3$)$_2$ | CHCl$_2$ | oil |
| 60 | H | 2,4(CH$_3$O)$_2$ | CH$_2$ | C$_3$H$_7$n | CHCl$_2$ | oil |
| 61 | H | 2,4(CH$_3$O)$_2$ | CH$_2$ | C$_2$H$_5$ | CHCl$_2$ | |
| 62 | H | 2,4(CH$_3$O)$_2$ | CH$_2$ | CH$_2$CH=CH$_2$ | CHCl$_2$ | |
| 63 | H | 2,4(CH$_3$O)$_2$ | CH$_2$ | CH$_2$CH(CH$_3$)$_2$ | CHCl$_2$ | |
| 64 | H | 2,4(CH$_3$O)$_2$ | CH$_2$ | CH(CH$_3$)C$_2$H$_5$ | CHCl$_2$ | |
| 65 | H | 2,4(CH$_3$O)$_2$ | CH$_2$CH$_2$ | CH(CH$_3$)$_2$ | CHCl$_2$ | |

Examples of formulations of active substances of the formula I or mixtures of these active substances with herbicides

EXAMPLE 4:

| | | | |
|---|---|---|---|
| Active substance of the formula I or mixture with a herbicide | 20% | 60% | 0.5% |
| Na ligninsulfonate | 5% | 5% | 5% |
| Na laurylsulfate | 3% | — | — |
| Na diisobutylnaphthalenesulfonate | — | 6% | 6% |
| Octylphenol polethylene glycol ether (7-8 moles of EO) | — | 2% | 2% |
| Highly dipserse silica | 5% | 27% | 27% |
| Kaolin | 67% | — | — |
| Sodium chloride | — | — | 59.5% |

The active substance is thoroughly mixed with the adjuvants and the mixture is thoroughly ground in a suitable mill. This gives wettable powders which can be diluted with water to give suspensions of any desired concentration.

EXAMPLE 5:

| | | |
|---|---|---|
| Active substance of the formula I or mixture with a herbicide | 10% | 1% |
| Octylphenol polyethylene glycol ether (4-5 moles of EO) | 3% | 3% |
| Ca dodecylbenzenesulfonate | 3% | 3% |
| Castor oil polyglycol ether (36 moles of EO) | 4% | 4% |
| Cyclohexanone | 30% | 10% |
| Mixed xylenes | 50% | 79% |

Emulsions of any desired concentration can be prepared from this concentrate by dilution with water.

EXAMPLE 6:

| | | |
|---|---|---|
| Active substance of the formula I or mixture with a herbicide | 0.1% | 1% |

-continued

| | | |
|---|---|---|
| Talc | 99.9 | — |
| Kaolin | — | 99% |

Ready-to-use dusts are obtained by mixing the active substance with the carrier and grinding the mixture on a suitable mill.

EXAMPLE 7:

| | | |
|---|---|---|
| Active substance of the formula I or mixture with a herbicide | 10% | 1% |
| Na ligninsulfonate | 2% | 2% |
| Carboxymethylcellulose | 1% | 1% |
| Kaolin | 87% | 96% |

The active substance is mixed with the adjuvants and the mixture is ground and moistened with water. This mixture is extruded and then dried in a stream of air.

EXAMPLE 8:

| | |
|---|---|
| Active substance of the formula I or mixture with a herbicide | 3% |
| Polyethylene glycol (MW 200) | 3% |
| Kaolin | 94% |

The active substance is finely ground and applied uniformly, in a mixer, to the kaolin, which has been moistened with polyethylene glycol. Dust-free coated granules are obtained in this way.

EXAMPLE 9:

| | | |
|---|---|---|
| Active substance of the formula I or mixture with a herbicide | 40% | 5% |
| Ethylene glycol | 10% | 19% |
| Nonylphenol polyethylene glycol ether (15 moles of EO) | 6% | 1% |
| Na ligninsulfonate | 10% | 5% |
| Carboxymethylcellulose | 1% | 1% |
| 37% strength aqueous formaldehyde solution | 0.2% | 0.2% |
| Silicone oil in the form of a 75% strength aqueous emulsion | 0.8% | 0.8% |
| water | 32% | 77% |

The active substance is finely ground and intimately mixed with the adjuvants. This gives a suspension concentrate from which suspensions of any desired concentration can be prepared by dilution with water.

EXAMPLE 10:

| | |
|---|---|
| Active substance of the formula I or mixture with a herbicide | 5% |
| Isopropylamine | 1% |
| Octylphenol polyethylene glycol ether (78 moles of EO) | 3% |
| water | 91% |

Biological Examples

The capacity of the compound of the formula I to protect cultivated plants against the phytotoxic action of strong herbicides can be seen from the following example. In the description of the test the compound of the formula I is described as the antidote (antidote).

EXAMPLE 11:

Test with herbicide and antidote in maize. Herbicide and antidote are applied together as a tank mixture by the pre-emergence technique.

Plastic containers (25 cm long × 17 cm wide × 12 cm high) are filled with sandy, loamy soil and sown with maize seeds of the variety LG 5. After the seeds have been covered, a dilute solution of one part of the substance to be tested as a safener and 4 parts of the herbicide, is sprayed onto the surface of the soil as a tank mixture in an application rate of 1 kg/ha of antidote and 4 kg/ha of herbicide. The protective action of the safener is evaluated as a percentage 21 days after the application. The references used here are the plants which have been treated only with the herbicide (no protective action) and the completely untreated control (100% protective action).

Test results:

Herbicide:
N-Chloroacetyl-N-(2-methoxy-1-methylethyl)2-methyl-6-ethylaniline ("metolachlor" 4 kg/ha)

| antidote 1 kg/ha | relative protective action |
|---|---|
| 1 | 75% |
| 2 | 75% |
| 3 | 75% |
| 4 | 75% |
| 5 | 75% |
| 8 | 63% |
| 12 | 75% |
| 14 | 63% |
| 15 | 38% |
| 16 | 38% |
| 17 | 75% |
| 18 | 63% |
| 19 | 50% |
| 26 | 63% |
| 32 | 63% |
| 34 | 63% |
| 37 | 50% |
| 44 | 50% |
| 45 | 50% |
| 46 | 63% |
| 49 | 63% |
| 50 | 63% |
| 51 | 75% |
| 58 | 75% |

EXAMPLE 12:

Test with herbicide and antidote in sorgho (millet). The antidote is applied as seed-dressing.

Millet seeds of the variety Funk G 522 are mixed with the antidote in a glass vessel. The seeds and the antidote are well mixed by shaking and rotating the glass vessel. The seeds which are thus treated are then sown into a plastic container of the following dimensions: 25 × 17 cm² area and 12 cm high. The seeds are covered with a thin layer of earth. Then the herbicide is sprayed as an aqueous emulsion in the desired concentration. The state of the plants is evaluated after 21 days and the protective action of the antidote is expressed in percents. The references used are the plants which have been treated with the herbicide alone (no protective action) and untreated control plants (normal growth or 100% protective action).

Test results:

Herbicide:
N-Chloroacetyl-N-(2-methoxy-1-methylethyl)2-methyl-6-ethylaniline ("metolachlor").

| antidote compound No. | application rate | herbicide application rate | relative protective action |
| --- | --- | --- | --- |
| 2 | 0.5 g/kg seed | 2 kg/ha | 38% |
| 15 | 0.5 g/kg seed | 2 kg/ha | 38% |
| 16 | 0.5 g/kg seed | 2 kg/ha | 38% |

I claim:

1. A composition for selectively controlling weeds in maize or sorghum which contains a herbicidally effective amount of metolachlor and for protecting the maize or sorghum from the phytotoxic action of the metolachlor a herbicidally antagonistically effective amount of an acylamide derivative of the formula

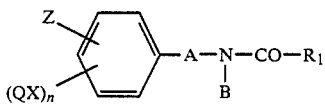

wherein
X is oxygen;
Q is $C_1$-$C_6$-alkyl, $C_2$-$C_6$-alkoxyalkyl or $C_3$-$C_6$-dialkoxyalkyl;
n is 1, 2 or 3;
Z is hydrogen;
A is $C_1$-$C_6$-alkylene which may be straight-chained or branched;
B is $C_1$-$C_6$-alkyl or $C_2$-$C_6$-alkenyl which is unsubstituted or substituted by $C_1$-$C_4$-alkoxy; and
$R_1$ is dichloromethyl, together with an inert agriculturally acceptable carrier and a surfactant.

2. The seed of sorghum which has been treated with a composition according to claim 1.

3. A composition according to claim 1, wherein Q is $C_1$-$C_6$-alkyl.

4. A composition according to claim 1, wherein n is 1 or 2.

5. A composition according to claim 1, wherein the group QX is methoxy.

6. A composition according to claim 1 wherein X is oxygen, Q is methyl, n is 1 or 2, A is $C_1$-$C_2$-alkylene, B is $C_1$-$C_4$-alkyl.

7. A composition according to claim 6 wherein the acylamide derivative is N-(3,4-dimethoxybenzyl)-N-isopropyl-dichloroacetamide.

8. As a wettable powder a composition according to claim 1 comprising from 0.5 to 90% by weight acylamide derivative, 5 to 95% by weight inert solid carrier, and 0.5 to 20% by weight surfactant.

9. A composition according to claim 8 comprising 1 to 80% by weight acylamide derivative, 15 to 90% carrier and 1 to 15% by weight surfactant.

10. As an emulsifiable concentrate a composition according to claim 1 comprising 1 to 20% by weight acylamide derivative, 5 to 30% by weight surfactant and 50 to 94% by weight inert liquid carrier.

11. A composition according to claim 10 comprising 5 to 10% by weight acylamide derivative, 10 to 20% by weight surfactant and 70 to 85% by weight carrier.

12. A composition according to claim 1 wherein B is $C_1$-$C_6$alkyl or $C_2$-$C_6$alkenyl.

13. A composition for selectively controlling weeds in cultures of maize and sorghum, which contains a herbicidally active amount of N-chloroacetyl-N-(2-methoxy-1-methylethyl)-2-ethyl-6-methylaniline and a herbicidally antagonistically effective amount of an acylamide derivative of the formula

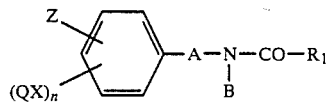

wherein X is oxygen, Q is $C_1$-$C_4$-alkyl or $C_2$-$C_4$-alkoxyalkyl, n is 1 or 2, A is a $C_1$-$C_4$-alkylene or $C_2$-$C_4$-alkenylene bridge, z is hydrogen, B is $C_1$-$C_6$-alkyl or $C_2$-$C_6$-alkenyl which is unsubstituted or substituted by $C_1$-$C_4$-alkoxy and $R_1$ is dichloromethyl, together with an inert agriculturally acceptable carrier and a surfactant.

* * * * *